US00PP25768P3

(12) United States Plant Patent
Scheffers

(10) Patent No.: US PP25,768 P3
(45) Date of Patent: Aug. 4, 2015

(54) *MEDINILLA* PLANT NAMED 'RS005'

(50) Latin Name: *Medinilla dolichophylla×magnifica*
Varietal Denomination: RS005

(71) Applicant: Robertus Scheffers, Monster (NL)

(72) Inventor: Robertus Scheffers, Monster (NL)

( * ) Notice: Subject to any disclaimer, the term of this patent is extended or adjusted under 35 U.S.C. 154(b) by 189 days.

(21) Appl. No.: 13/987,200

(22) Filed: Jul. 9, 2013

(65) Prior Publication Data

US 2015/0020258 P1 Jan. 15, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Cassandra Bright

(57) ABSTRACT

A new and distinct *Medinilla* cultivar named 'RS005' is disclosed, characterized by large pink bracts, large green leaves and suitability for commercial production. The new variety is a *Medinilla*, normally produced as an ornamental plant.

1 Drawing Sheet

Latin name of the genus and species: *Medinilla dolichophylla×magnifica.*

Variety denomination: 'RS005'.

BACKGROUND OF THE INVENTION

The new *Medinilla* cultivar is a product of a planned breeding program conducted by the inventor, Robertus H. M. Scheffers, in Monster, Netherlands. The objective of the breeding program was to produce new *Medinilla* varieties for ornamental commercial applications. The new variety is a product of crossbreeding that occurred during 2008, at a commercial nursery in Monster, Netherlands.

The seed parent is an unpatented, unnamed variety of *Medinilla dolichophylla*. The pollen parent is an unpatented, unnamed variety *Medinilla magnifica*. The new variety was discovered in 2009 by the inventor in a group of seedlings resulting from the 2008 crossing, in a commercial nursery in Monster, Netherlands.

Asexual reproduction of the new cultivar has been performed by vegetative cuttings. This was first performed at a commercial nursery in Monster, Netherlands in 2010 and has shown that the unique features of this cultivar are stable and reproduced true to type in successive generations.

SUMMARY OF THE INVENTION

The cultivar 'RS005' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RS005'. These characteristics in combination distinguish 'RS005' as a new and distinct *Medinilla* cultivar:

1. Large inflorescence with pink bract coloration.
2. Large green leaves.
3. Suitability for commercial production.

PARENT COMPARISON

Plants of the new cultivar 'RS005' are similar to plants of the seed parent, *Medinilla Dolichophylla* in most horticultural characteristics, however, plants of the new cultivar 'RS005' produce a different leaf shape than the seed parent. Additionally, 'RS005' also produces a flower of darker pink coloration than those of the seed parent.

Plants of the new cultivar 'RS005' are similar to plants of the pollen parent; *Medinilla magnifica* in most horticultural characteristics, however, plants of the new cultivar 'RS005' produces double flowers whereas the pollen parent produces a single flower. 'RS005' also produces shorter petioles and smaller leaves compared to the pollen parent.

COMMERCIAL COMPARISON

Plants of the new cultivar 'RS005' are best compared to *Medinilla* 'RS003', filed concurrently. While the two cultivars are similar in most horticultural characteristics, 'RS005' differs from 'RS003' in the following characteristics;

1. 'RS005' has longer lateral branches.
2. 'RS005' has smaller foliage.
3. Foliage of 'RS005' has more greyed-green coloration not found on foliage of 'RS003'.
4. 'RS005' has larger inflorescence with longer peduncles.
5. Inflorescence of 'RS005' have less individual flowers than inflorescence of 'RS003'.
6. Flower bracts of 'RS005' are smaller than bracts of 'RS003'.

BRIEF DESCRIPTION OF THE PHOTOGRAPH

The accompanying photograph in FIG. 1 illustrates in full color a close up of typical flowers and foliage of 'RS005'.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RS005' plants grown outdoors in Monster, Netherlands. The growing temperature ranged from 20° C. to 23° C. during the day and from 20° C. to 23° C. during the night. General light conditions are bright, normal sunlight. Measurements and numerical values represent averages of typical plant types.

Botanical classification: *Medinilla dolichophylla×magnifica* 'RS005'.

PROPAGATION

Time to initiate roots: Summer: 21 to 28 days at approximately 20-23° C. Winter: 28 to 35 days at approximately 20-23° C.

Root description: Moderately dense, non-fleshy, non-fibrous, moderately thick, colored Near Greyed-Orange RHS N170A and N170B.

PLANT

Age of plant described: From 50 weeks from a rooted cutting.

Growth habit: Spreading-upright, overall plant shape: flattened globular.

Pot size of plant described: 2 liter circular pot.

Height: 36.0 cm.

Plant spread: At widest: 75.0 cm, at narrowest: 38.5 cm.

Growth rate: Moderate.

Branching characteristics: Not very free branching.

Quantity of primary lateral branches: Average: 3.

Characteristics of primary lateral branches:

*Length*.—Average 27.0 cm.

*Diameter*.—Lateral branches flattened, average diameter at widest: 1.5 cm, average diameter at narrowest: 0.7 cm.

*Color*.—Near Yellow-Green; RHS 144A, margins (of flattened branches) Near Greyed-Yellow RHS 162A.

*Texture*.—Glabrous, moderately glossy, flattened margins wavy.

*Strength*.—Strong.

Internode length: Average: 13.9 cm.

FOLIAGE

Leaf:

*Arrangement*.—Opposite.

*Shape*.—Ovate.

*Quantity*.—Approximately 4 per branch (2 pairs).

*Average overall length*.—Average: 25.1 cm.

*Average overall width*.—Average: 13.3 cm.

*Apex*.—Short apiculate to mucronulate.

*Base*.—Truncate.

*Margin*.—Entire, undulate.

*Texture of top surface*.—Glabrous, veins furrowed.

*Texture of lower surface*.—Glabrous, ridges due to furrowed venation.

*Appearance*.—Leathery, shiny.

*Aspect*.—Slightly carinate, margins undulate.

*Color*.—Young foliage upper side: Near Yellow-Green RHS 146B. Young foliage under side: Near Green to Yellow-Green; in between RHS 143B and 144A. Mature foliage upper side: Near Yellow-Green to Greyed-Green; in between RHS 147A and N189A but darker. Mature foliage under side: Near Yellow-Green RHS 147D.

*Venation*.—Type: Camptodrome. Venation color upper side: Near Yellow-Green; in between RHS 144B and 145A. Venation color under side: Near Yellow-Green RHS 146D.

*Petiole*.—No petioles present, leaves sessile.

*Stipule description*.—No stipules present.

FLOWER

Natural flowering season: April to June in the Philippines.

Typical commercial flowering technique and time: To get the plant into flowering, keep the plant at 18 degrees Celsius for about ten weeks. Year around flowering occurs under the condition plants receive this cold treatment.

Days to flowering from rooted cutting: 50 weeks.

Inflorescence and flower type and habit: Panicle.

Rate of flower opening: 13 to 16 weeks from bud to fully opened flower.

Flower longevity on plant: Approximately 20 weeks of flowering from first buds to exhausted flowering.

Persistent or self-cleaning: Self-cleaning.

Inflorescence:

*Length*.—Average: 18.0 cm.

*Diameter*.—Average: 14.3 cm.

*Aspect*.—Pendulous.

*Number of flowers*.—Per inflorescence, average: 160.

Bud:

*Shape*.—Obovate.

*Length*.—Average: 0.6 cm.

*Diameter*.—Average: 0.4 cm.

*Color*.—Near Red-purple to greyed-purple; in between RHS 58D and 186C.

Flower size:

*Diameter*.—Average: 0.7 cm.

*Depth*.—Average: 1.1 cm.

*Aspect*.—Pendulous.

Petals:

*Quantity*.—5.

*Arrangement*.—Rotate, fused and part of an urn-shaped hypanthium consisting of calyx, corolla, androecium and gynoecium.

*Length*.—Average: 0.5 cm.

*Width*.—Width cannot be measured, petals fused to a urn-shaped hypanthium and only visible when cut lengthways.

*Apex*.—Fused to the top of the urn-shaped hypanthium.

*Base*.—Fused to the urn-shaped hypanthium.

*Margin*.—Margin cannot be seen, petals fused to a urn-shaped hypanthium and only visible when cut lengthways.

*Texture, upper and lower surfaces*.—Glabrous.

*Appearance*.—Matte.

*Color*.—When opening, upper surface: Near Greyed-Purple RHS 186B. When opening, lower surface: Near Greyed-Purple RHS 186B. Fully opened, upper surface: Near Greyed-Purple RHS 186B. Fully opened, lower surface: Near Greyed-Purple RHS 186B. Aging: Not fading.

Sepals:

*Arrangement*.—Rotate, fused and part of an urn-shaped hypanthium consisting of calyx, corolla, androecium and gynoecium.

*Quantity*.—5.

*Length*.—0.9 cm.

*Width*.—Since sepals cannot be seen as separate sepals, width, shape, apex, base and margin cannot be seen/measured.

*Shape*.—Since sepals cannot be seen as separate sepals, width, shape, apex, base and margin cannot be seen/measured.

*Apex*.—Since sepals cannot be seen as separate sepals, width, shape, apex, base and margin cannot be seen/measured.

*Base*.—Since sepals cannot be seen as separate sepals, width, shape, apex, base and margin cannot be seen/measured.

*Margin*.—Since sepals cannot be seen as separate sepals, width, shape, apex, base and margin cannot be seen/measured.

*Color, interior and exterior*.—Near Red-Purple RHS 58A, top on exterior Near Yellow-Green RHS 150D.

Bracts:

*Arrangement*.—At the base of each pair of secondary peduncles, four bracts are present.

*Quantity*.—32.

*Length*.—Average: 6.4 cm

*Width*.—Average: 3.6 cm.

*Shape*.—Ovate.

*Apex*.—Acute.

*Base*.—Truncate.

*Margin*.—Entire.

*Color, immature, interior*.—Near Yellow-green RHS 150D, veins and top tinged Near Red-Purple RHS 58A and 58B.

*Color, immature, exterior*.—Near Yellow-green RHS 150D, veins and top tinged Near Red-Purple RHS 58C.

*Color, mature, interior*.—Near Red-Purple RHS 63B and 63C, tinged Near Yellow-Green towards the margins and top; in between RHS 145A and 146D. Veins Near Red-Purple RHS 61C.

*Color, mature, exterior*.—Near Red-purple RHS 59D, tinged Near Yellow-Green towards the margins and top; in between RHS 145A and 146D. Veins Near Red-Purple RHS 61B.

Peduncles:

*Length*.—Average: 31.7 cm.

*Diameter*.—Peduncles flattened quadrangulate, average diameter at widest: 0.8 cm, average diameter at narrowest: 0.4 cm.

*Angle*.—Peduncle straight on top of lateral branch, but due to the weight of the inflorescence the peduncle is bend to straight vertical (about 90° to soil level/horizontal).

*Strength*.—Very strong.

*Texture*.—Glabrous, matte.

*Color*.—Near Yellow-Green RHS 145B and 145C, tinged and margins (peduncle quadrangular) Near Red-Purple; N57A and 58A. Secondary peduncles Near Red-Purple RHS 58B.

Pedicels:

*Length*.—Average: 0.6 cm.

*Diameter*.—Average: 0.2 cm.

*Angle*.—About 40° to peduncle.

*Strength*.—Moderately strong.

*Texture*.—Glabrous, matte.

*Color*.—Near Red-purple RHS 58C.

Fragrance: No fragrance.

REPRODUCTIVE ORGANS

Stamens:

*Number*.—Average: 10.

*Length*.—Approximately 0.6 cm.

*Color*.—Near Purple-Violet RHS N81A.

Anthers:

*Shape*.—Basifixed, narrow obovate.

*Length*.—Approximately 0.2 cm.

*Color*.—Near Green-Yellow RHS 1A.

*Pollen*.—No pollen detected.

Pistil:

*Position*.—In the center of each flower, surrounded by stamen.

*Number*.—Average: 1.

*Length*.—Average: 0.4 cm.

*Style*.—Length: Average: 0.4 cm. Color: Near Yellow-Green RHS 146C and 146D.

*Stigma*.—Shape: Pointed. Color: Near Yellow-Green RHS 146D. Ovary Color: Near Yellow-Green RHS 146D.

OTHER CHARACTERISTICS

Seeds and fruits: No seeds-fruits detected to date.

Disease/pest resistance: Neither Resistance nor susceptibility to normal diseases and pests of the Genus observed.

Temperature tolerance: 10° C. to 30° C. temperature tolerance range.

What is claimed is:

1. A new and distinct cultivar of *Medinilla* plant named 'RS005' as herein illustrated and described.

* * * * *

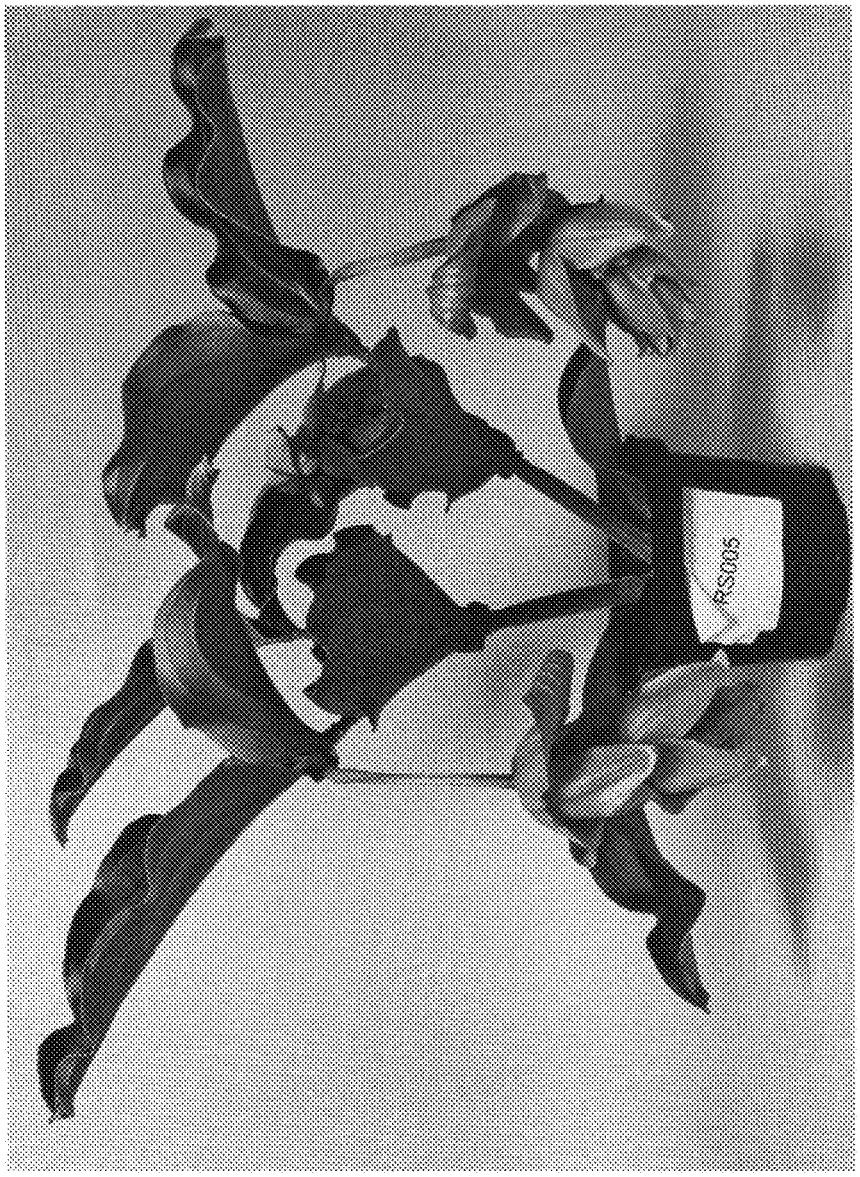
RS005